(12) United States Patent
Li et al.

(10) Patent No.: US 9,999,253 B2
(45) Date of Patent: Jun. 19, 2018

(54) ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Changzheng Dai, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days. days.

(21) Appl. No.: 15/356,640

(22) Filed: Nov. 20, 2016

(65) Prior Publication Data

US 2017/0065001 A1    Mar. 9, 2017

(30) Foreign Application Priority Data

Nov. 23, 2015 (CN) ...................... 2015 2 0932400 U

(51) Int. Cl.
| | |
|---|---|
| *A24F 13/00* | (2006.01) |
| *A24F 17/00* | (2006.01) |
| *A24F 25/00* | (2006.01) |
| *A24F 47/00* | (2006.01) |
| *F16K 15/14* | (2006.01) |
| *F22B 1/28* | (2006.01) |

(52) U.S. Cl.
CPC ............ *A24F 47/008* (2013.01); *F16K 15/14* (2013.01); *F22B 1/284* (2013.01)

(58) Field of Classification Search
CPC ...... A24F 47/002; A24F 47/008; A61M 11/04
USPC .......................................................... 131/329
See application file for complete search history.

(56) References Cited

U.S. PATENT DOCUMENTS

| | | | |
|---|---|---|---|
| 2012/0138054 A1* | 6/2012 | Hearn | A24F 47/002 128/203.12 |
| 2015/0230522 A1* | 8/2015 | Horn | A24F 47/008 131/329 |
| 2015/0282530 A1* | 10/2015 | Johnson | A61M 15/06 392/387 |
| 2016/0007654 A1* | 1/2016 | Zhu | A24F 47/008 131/328 |
| 2016/0128384 A1* | 5/2016 | Luciani | A24F 47/008 131/329 |
| 2016/0128385 A1* | 5/2016 | Lin | A24F 47/002 131/328 |
| 2016/0286860 A1* | 10/2016 | Flayler | A24F 47/008 |
| 2017/0050779 A1* | 2/2017 | Loritz | A61J 1/14 |

(Continued)

*Primary Examiner* — Abdullah Riyami
*Assistant Examiner* — Thang Nguyen
(74) *Attorney, Agent, or Firm* — Cheng-Ju Chiang

(57) ABSTRACT

The present disclosure relates to an atomizer for an electronic cigarette. The atomizer includes a housing, a liquid chamber, an atomizing unit, and a deformable valve. The liquid chamber is in the housing and configured for storing tobacco liquid. The liquid chamber has a liquid injecting opening. The atomizing unit is configured for absorbing and atomizing the tobacco liquid. The deformable valve is arranged in the liquid injecting opening. The valve is capable of being pushed open by an external injector, so that the tobacco liquid can be injected into the liquid chamber. The valve is capable of restoring to its original shape to seal the liquid injecting opening when the injector is removed.

9 Claims, 6 Drawing Sheets

(56) References Cited

U.S. PATENT DOCUMENTS

| | | | |
|---|---|---|---|
| 2017/0056368 A1* | 3/2017 | Hearn | A61M 11/02 |
| 2017/0156408 A1* | 6/2017 | Li | A24F 47/008 |
| 2017/0238605 A1* | 8/2017 | Matsumoto | A24F 47/002 |
| 2017/0238617 A1* | 8/2017 | Scatterday | A24F 47/008 |

* cited by examiner

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

A refillable electronic cigarette is becoming more and more popular because it is environmental-friendly. When tobacco liquid in the refillable electronic cigarette is used up, the user of the electronic cigarette usually uses an injector to fill in tobacco liquid. However, during this process, the tobacco liquid may leak out. For example, since the injector is not fixedly coupled with the electronic cigarette, the tobacco liquid may leak when the electronic cigarette is turned over, thus rendering user experience unsatisfactory.

What are needed, therefore, are an atomizer and an electronic cigarette using same, which can overcome the above shortcomings.

SUMMARY

The present disclosure relates to an atomizer for an electronic cigarette. The atomizer includes a housing, a liquid chamber, an atomizing unit, and a deformable valve. The liquid chamber is in the housing and configured for storing tobacco liquid. The liquid chamber has a liquid injecting opening. The atomizing unit is configured for absorbing and atomizing the tobacco liquid. The deformable valve is arranged in the liquid injecting opening. The valve is capable of being pushed open by an external injector, so that the tobacco liquid can be injected into the liquid chamber. The valve is capable of restoring to its original shape to seal the liquid injecting opening when the injector is removed.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
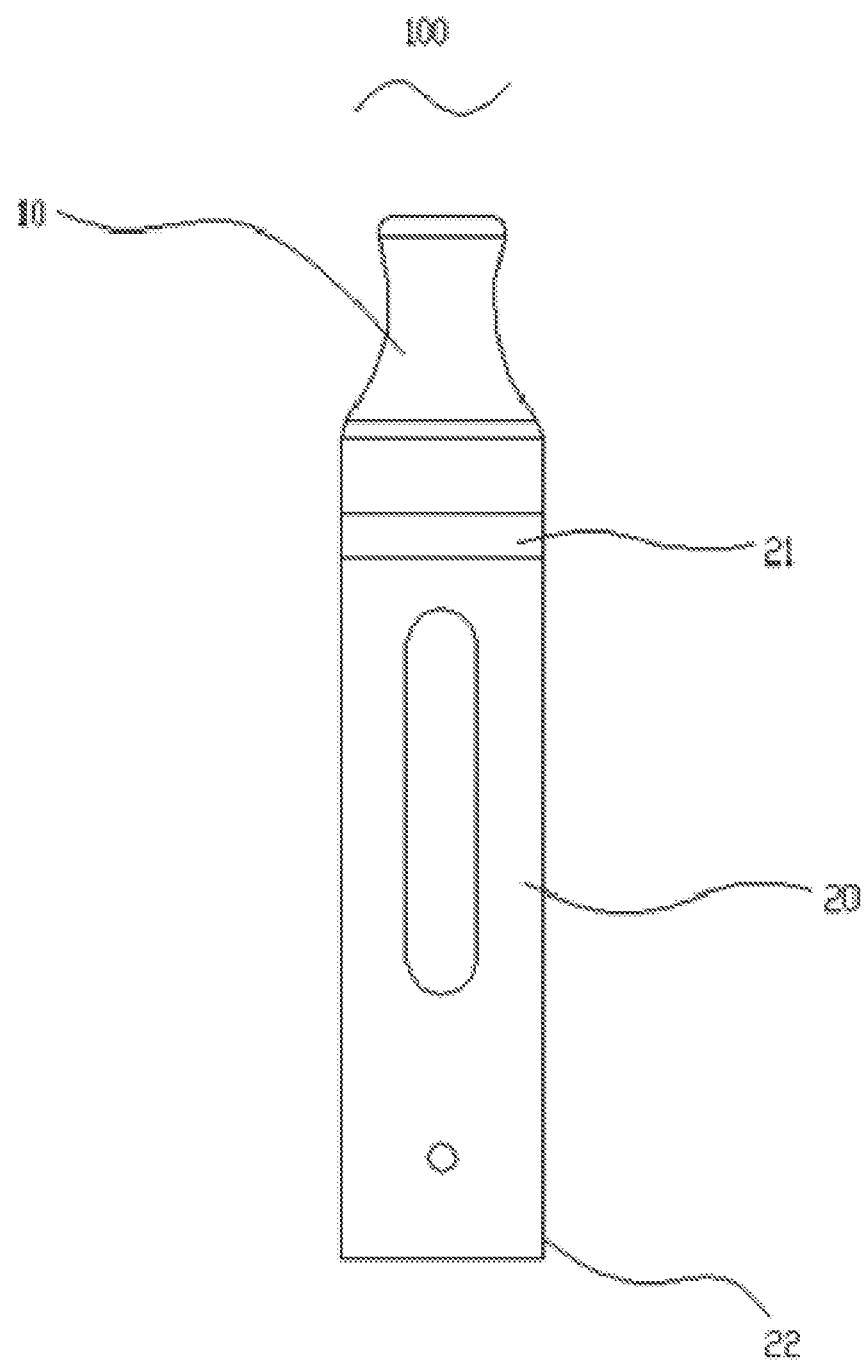
FIG. 1 is a side view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
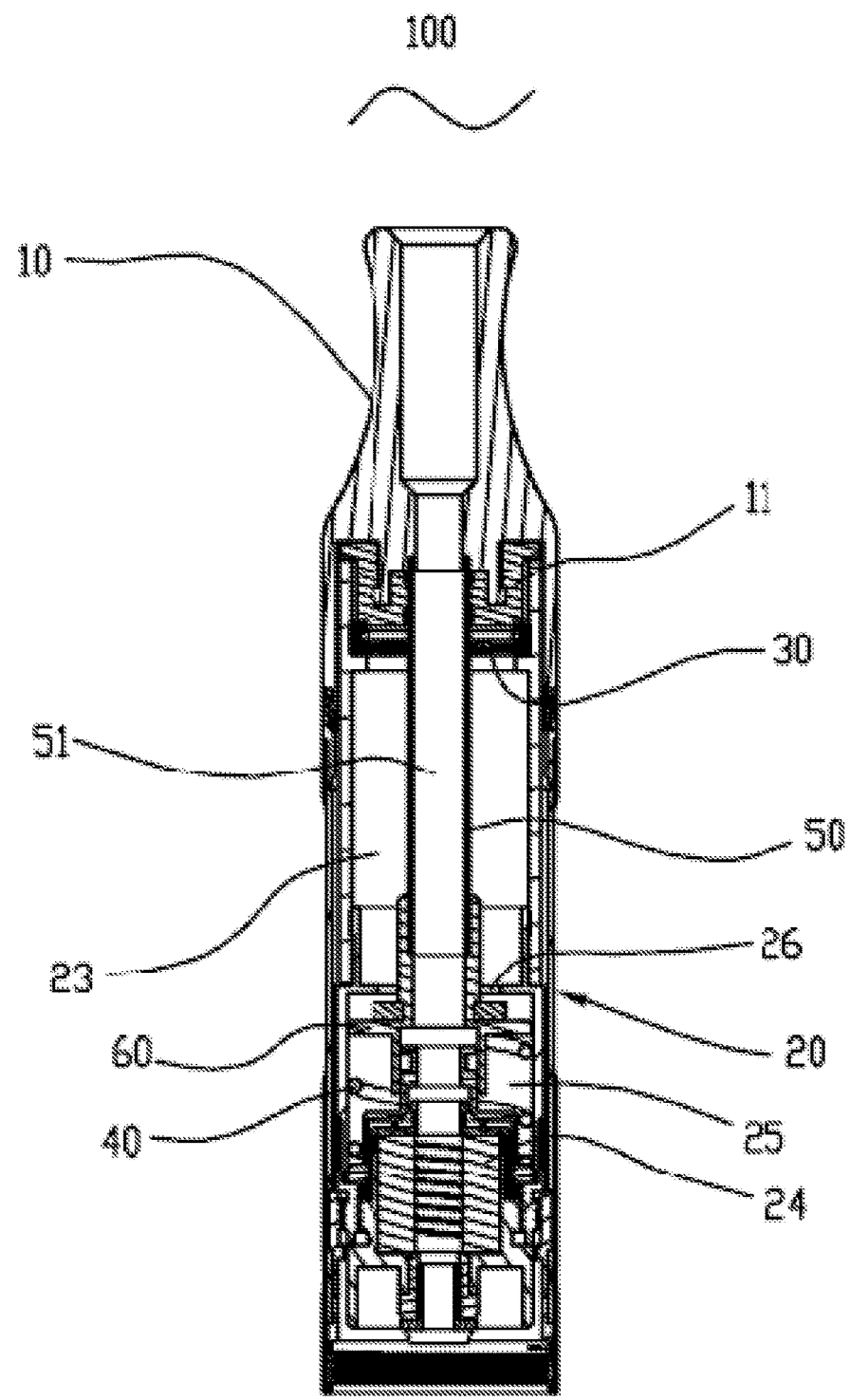
FIG. 2 is a cross-sectional view of the atomizer of FIG. 1.
Figure 3:
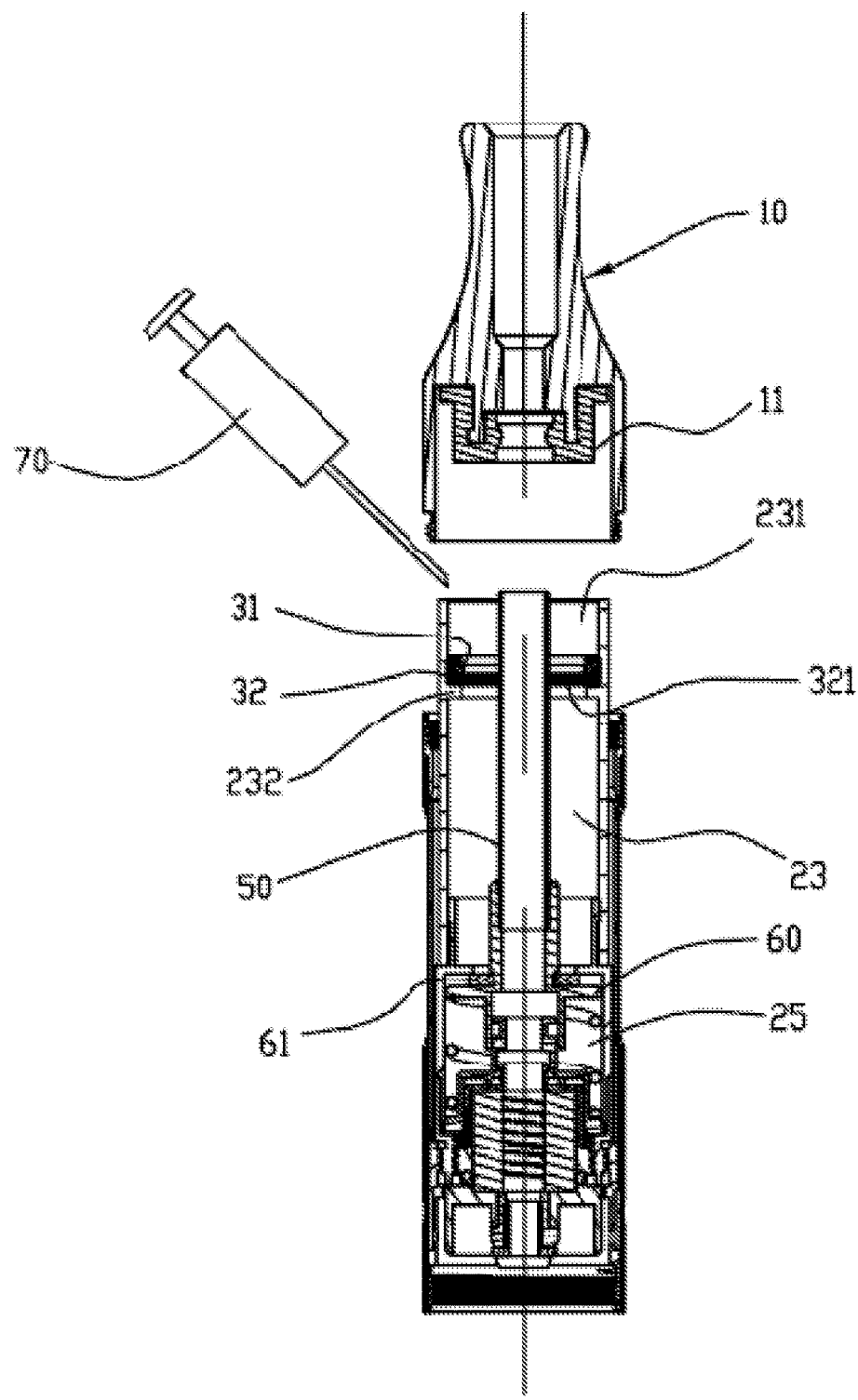
FIG. 3 is an exploded cross-sectional view of FIG. 1 according to a first embodiment.

Referring to FIGS. 1-3, an atomizer 100 includes a housing 20, a liquid chamber 23 defined in the housing 20, and an atomizing unit 24. The atomizing unit 24 is configured (i.e., structured and arranged) for absorbing and atomizing tobacco liquid in the liquid chamber 23. The housing 20 includes a first end 21 and an opposite second end 22. The first end 21 defines a liquid injecting opening 231 in communication with the liquid chamber 23. The second end 22 is configured for connecting with a power supply 200. A deformable valve 30 is arranged in the liquid injecting opening 231. The valve 30 is capable of being pushed open by an external liquid injector 70, such that tobacco liquid can be filled into the liquid chamber 23. When the liquid injector 70 is moved out from the liquid injecting opening 231, the valve 30 restores to its original shape, and seals the liquid injecting opening 231.

A mouthpiece 10 is detachably connected with an end of the housing adjacent to the liquid injecting opening 231. A liquid stopper 11 is provided in the mouthpiece 10, and is configured for further sealing the liquid injecting opening 231. An air pipe 50 is provided in the housing 20, and the air pipe 50 defines an air passage 51. One end of the air pipe 50 is connected with the atomizing unit 24, and the other end of the air pipe 50 is in communication with the mouthpiece 10. The valve 30 sleeves the air pipe 231.

Referring to FIG. 2, a movable element 60 is connected with an end of the air pipe 50, which is connected with the atomizing unit 24. An elastic element 40 abuts against the movable element 60. The elastic element 40 is capable of driving the movable element 60 to abut against the mouthpiece 10. The elastic element 40 is configured to drive the air pipe 50 and the movable element 60 to move axially, when the mouthpiece 10 is detached. In the present embodiment, an end of the air pipe 50 is connected with the liquid stopper 11, and the air pipe 50 is in communication with the atomizing unit 24 via the movable element 60.

Referring to FIGS. 2-3, the valve 30 includes a fixing element 31 and a flexible element 32. The flexible element 32 is pressed against an inner wall of the housing 20 by the fixing element 31. A main body of the flexible element 32 extends inwards along a radial direction of the housing 20 to form a deformable part 321. The deformable part 321 is capable of being pushed open by the external liquid injector 70. The flexible element 32 is made of silicone. A step portion 232 is arranged in the liquid injecting opening 231. In the present embodiment, the deformable part 321 and the fixing element 31 rests on top of the step portion 232.

Referring to FIGS. 2-3, a buffer chamber 25 is arranged below the liquid chamber 23. A liquid hole 26 is defined between the buffer chamber 25 and the liquid chamber 23. A sealing ring 61 is provided nesting the movable element 60. The sealing ring 61 is capable of moving axially together with the movable element 60 to seal or open the liquid hole 26. The atomizing unit 24 is disposed in the buffer chamber 25. The atomizing unit 24 can absorb tobacco liquid from the buffer chamber 25 and atomize the tobacco liquid. When the mouthpiece 10 is detached, the elastic element 40 is capable of driving the movable element 60 to move axially, such that the sealing ring 61 seals the liquid hole 26. In this way, tobacco liquid is prevented from flowing into the buffer chamber 25 during liquid injecting process, thus reducing risk of liquid leakage.

Figure 4:
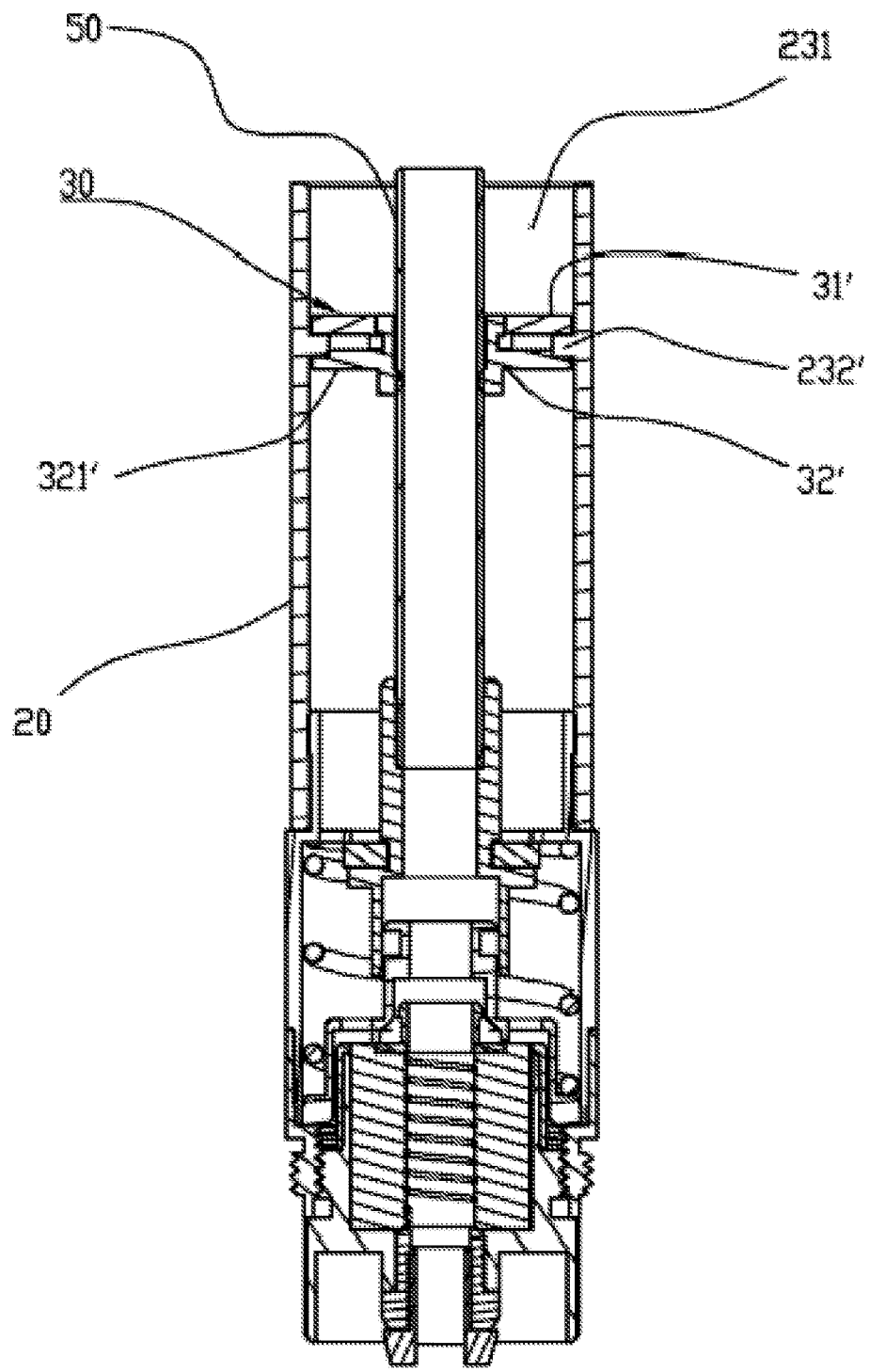
FIG. 4 is a cross-sectional view of part of an atomizer according to a second embodiment.
Figure 5:
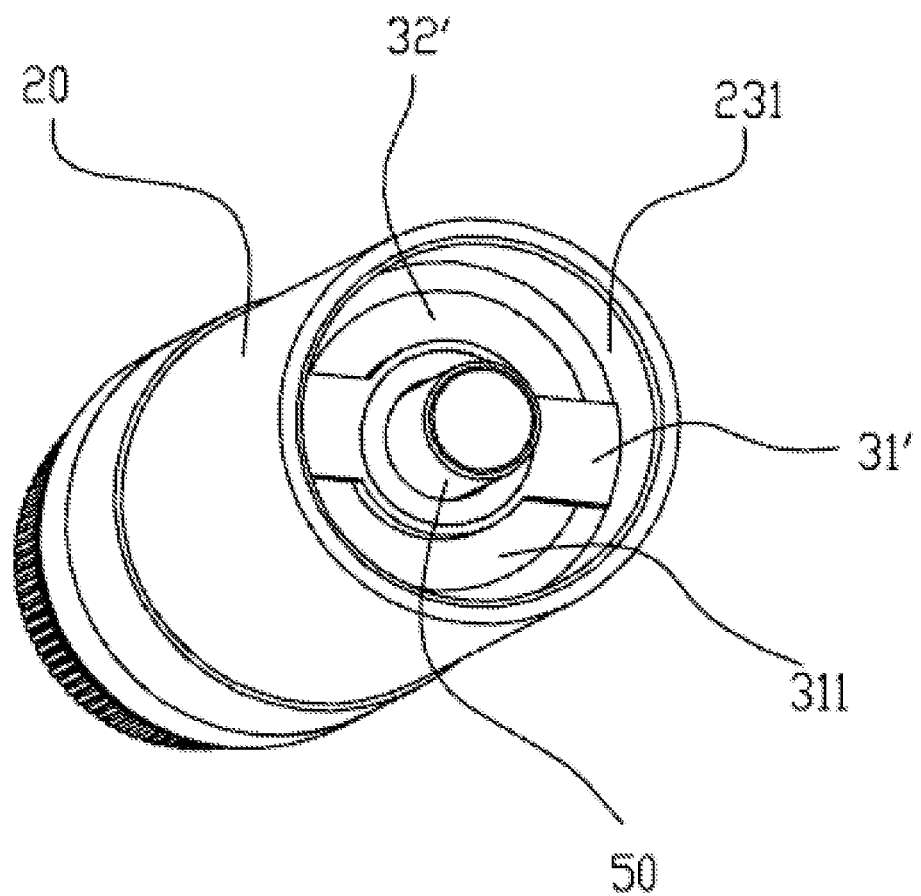
FIG. 5 is a perspective view of part of an atomizer of FIG. 4.

Referring to FIGS. 4-5, as an alternative embodiment, the valve 30 includes a fixing element 31' and a flexible element 32'. A step portion 232' is formed in the liquid injecting opening 231. The fixing element 31' is arranged on top of the step portion 232', and the flexible element 32' is positioned below the step portion 232'. A central part of the flexible element 32' is connected with a central part of the fixing element 31'. The fixing element 31' defines at least one opening 311, through which the injector 70 can push the flexible element 32' open. A main body of the flexible element 32' extends outwards in a radial direction to form a flexible part 321'.

Figure 6:
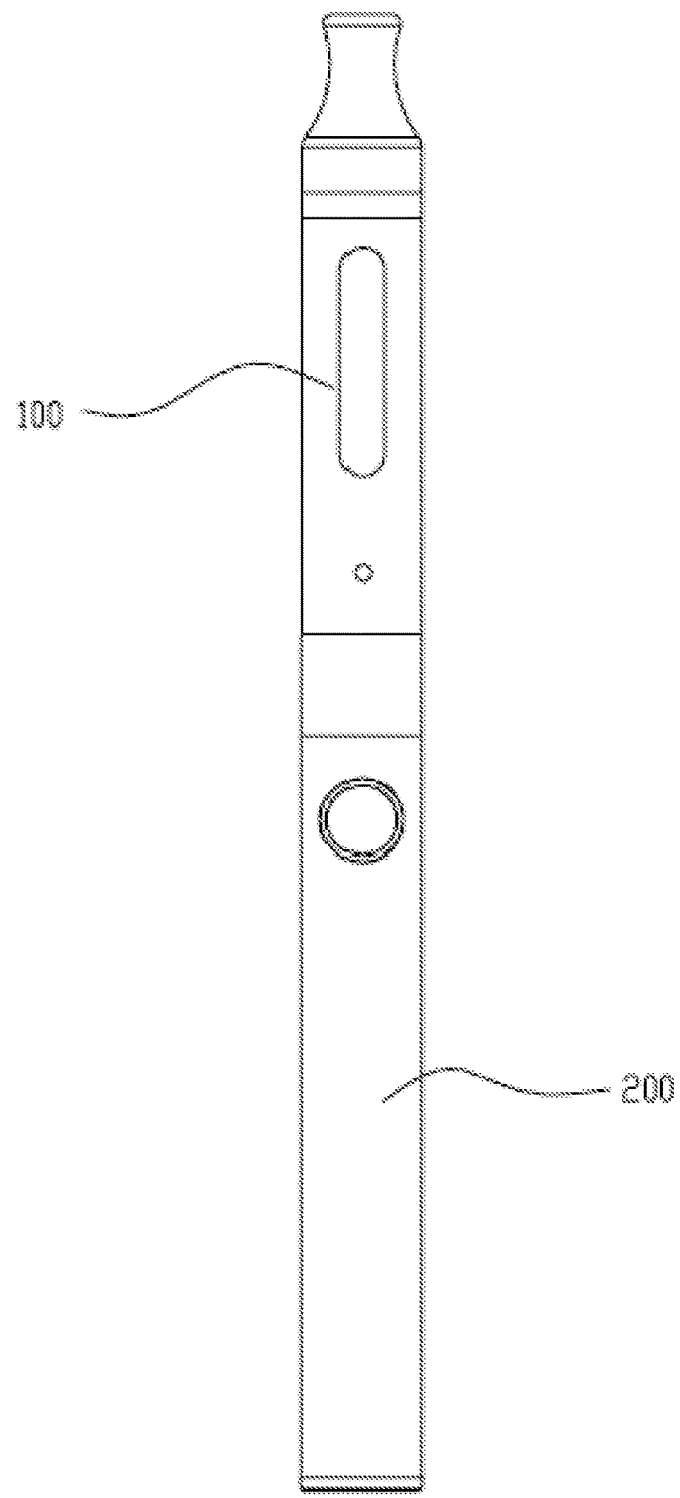
FIG. 6 is a side view of an electronic cigarette according to a third embodiment.

Referring to FIG. 6, an electronic cigarette includes the atomizer 100 and a power supply 200. The atomizer 100 and the power supply 200 are coupled by screw threads. The power supply 200 is configured for feeding the atomizer 100 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for an electronic cigarette, comprising:
a housing;
a liquid chamber in the housing and being configured for storing tobacco liquid, the liquid chamber having a liquid injecting opening;
an atomizing unit configured for absorbing and atomizing the tobacco liquid; and
a deformable valve arranged in the liquid injecting opening, the valve being capable of being pushed open by an external injector, so that the tobacco liquid can be injected into the liquid chamber, and the valve being capable of restoring to its original shape to seal the liquid injecting opening when the injector is removed;
wherein the valve comprises a fixing element and a flexible element, the flexible element is pressed against an inner wall of the housing by the fixing element, the fixing element defines an opening, the flexible element has a main body, and the main body extends in a radial direction inwardly to form a deformable part.

2. The atomizer according to claim 1, further comprising a mouthpiece detachably connected with the housing adjacent to the liquid injecting opening, wherein the mouthpiece comprises a liquid stopper for further sealing the liquid injecting opening.

3. The atomizer according to claim 2, further comprising an air pipe, wherein an end of the air pipe is in communication with the atomizing unit, and an opposite end of the air pipe is connected with the mouthpiece.

4. The atomizer according to claim 3, further comprising a movable element and an elastic element, wherein the movable element is connected with an end of the air pipe adjacent to the atomizing unit, the elastic elements abuts against the movable element, the elastic element is capable of driving the movable element to abut against the mouthpiece, and driving the air pipe and the movable element to move axially when the mouthpiece is detached.

5. The atomizer according to claim 4, further comprising a buffer chamber below the liquid chamber, wherein a liquid hole is defined between the buffer chamber and the liquid chamber, the atomizer further comprises a sealing ring nesting the movable element, and the sealing ring is axially movable together with the movable element to seal or open the liquid hole.

6. The atomizer according to claim 1, wherein the atomizing unit is arranged in the liquid chamber, such that the atomizing unit can absorb tobacco liquid from the buffer chamber.

7. The atomizer according to claim 1, wherein the housing further comprises a step portion in the liquid injecting opening, and the flexible element and the fixing element are arranged on the step portion.

8. An electronic cigarette, comprising:
an atomizer according to claim 1; and
a power supply configured for supplying the atomizer power.

9. An atomizer for an electronic cigarette comprising:
a housing;
a liquid chamber in the housing and being configured for storing tobacco liquid, the liquid chamber having a liquid injecting opening;
an atomizing unit configured for absorbing and atomizing the tobacco liquid; and
a deformable valve arranged in the liquid injecting opening, the valve being capable of being pushed open by an external injector, so that the tobacco liquid can be injected into the liquid chamber, and the valve being capable of restoring to its original shape to seal the liquid injecting opening when the injector is removed;
wherein the valve comprises a fixing element and a flexible element, the housing further comprises a step portion, the fixing element is positioned on the step portion, the flexible element is arranged below the step portion, a central part of the flexible element is connected with that of the fixing element, the fixing element defines an opening, the flexible element has a main body extending in a radial direction outwards to form a deformable part.

* * * * *